United States Patent [19]

Langer et al.

[11] 4,184,493
[45] Jan. 22, 1980

[54] CIRCUIT FOR MONITORING A HEART AND FOR EFFECTING CARDIOVERSION OF A NEEDY HEART

[75] Inventors: Alois A. Langer, Pittsburgh; Marlin S. Heilman, Gibsonia, both of Pa.; Morton M. Mower, Baltimore, Md.; Mieczyslaw Mirowski, 2405 Velvet Valley Way, Owings Mills, Md. 21117

[73] Assignee: Mieczyslaw Mirowski, Owings Mills, Md.

[21] Appl. No.: 878,006

[22] Filed: Feb. 15, 1978

Related U.S. Application Data

[63] Continuation-in-part of Ser. No. 620,025, Sep. 30, 1975, abandoned.

[51] Int. Cl.² .............................................. A61N 1/36
[52] U.S. Cl. ................................................ 128/419 D
[58] Field of Search ............... 128/2.06 A, 2.06 B, 128/2.06 R, 2.1 Z, 419 D

[56] References Cited

U.S. PATENT DOCUMENTS 3,587,563  6/1971  Ragsdale ........................ 128/2.06 A
3,861,387  1/1975  Lawhorn et al. ............... 128/2.06 A

OTHER PUBLICATIONS

Stratbucker et al., "Rocky Mountain Engineering Society" 1965, pp. 57-61.

Primary Examiner—William E. Kamm
Attorney, Agent, or Firm—Fleit & Jacobson

[57] ABSTRACT

Disclosed are two embodiments of a circuit for analyzing the ECG signals of a heart and for delivering a cardioverting pulse of energy to the heart if the heart is in an arrhythmic state in need of cardioversion. In the first embodiment, the ECG is filtered by a high pass filter to provide the derivative of the ECG, is reviewed by a window detector to determine the average time that the input ECG spends at high slope, and then the average occurrence of high slope segments is compared with a predetermined reference to determine whether the ECG is normal. Cardioversion is effected if the ECG is abnormal. In the second embodiment, an absolute value circuit and a level comparator is used in place of the window detector. The input ECG is normalized by an automatic gain control where the AGC voltage is derived from the ECG signals after high pass filtration.

16 Claims, 20 Drawing Figures

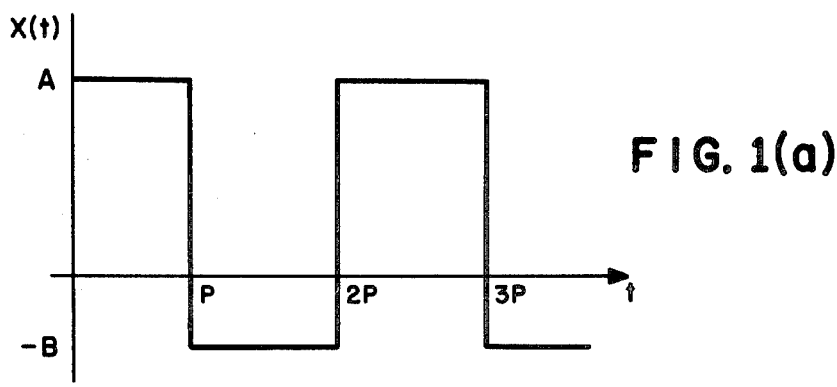
FIG. 1(a)
FIG. 1(b)
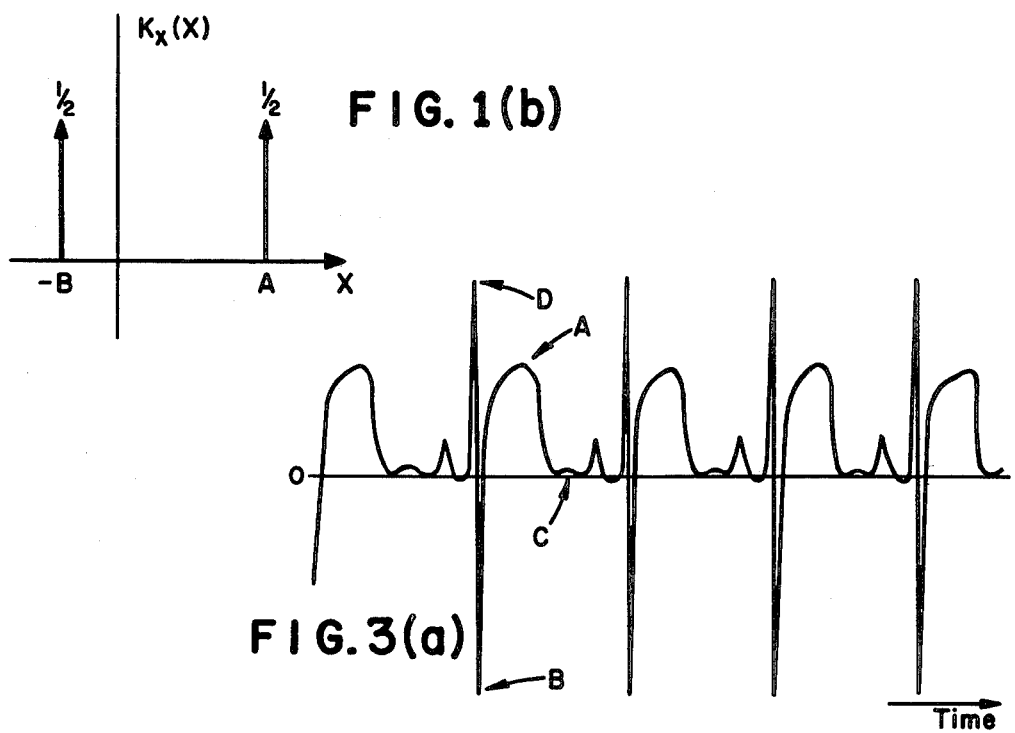
FIG. 3(a)
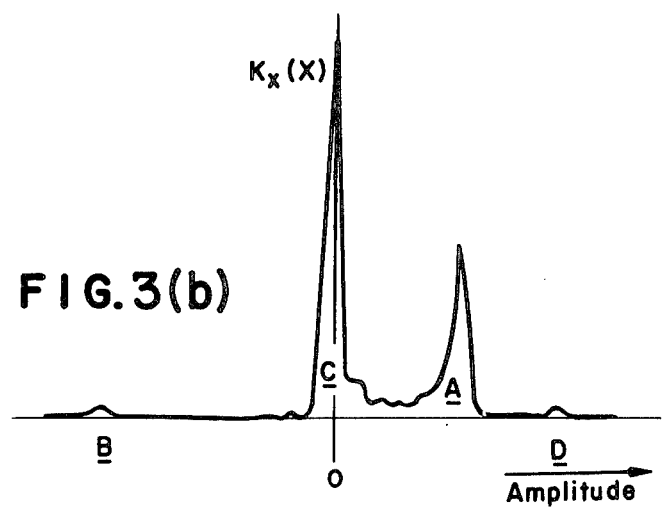
FIG. 3(b)

CIRCUIT FOR MONITORING A HEART AND FOR EFFECTING CARDIOVERSION OF A NEEDY HEART

REFERENCE TO RELATED APPLICATION

This is a continuation-in-part of U.S. Application Ser. No. 620,025, filed on Sept. 30, 1975, and now abandoned. The subject matter from the parent application which is not embodied herein, is embodied in divisional U.S. Application Ser. No. 878,005, filed on even date herewith.

BACKGROUND OF THE INVENTION

Ventricular fibrillation (VF) is a lethal cardiac arrhythmia for which the only known efficacious treatment is electrical countershock. A victim of VF outside of the hospital setting has little chance of survival since treatment must take place within a few minutes after the onset of the episode.

Fortunately, new techniques and devices are being devised to help deal with this life threatening condition. Among these are computer techniques which aid in the identification of high risk VF patients, anti-arrhythmic drugs which can prophylactically be administered to these patients, programs for wide-spread cardiopulmonary resuscitation training, and implantable devices which can automatically detect VF and deliver cardioverting countershocks.

"Cardioverting" or "cardioversion" as used herein is intended to encompass the correction of a number of arrhythmic heat conditions, both lethal and non-lethal. Those arrhythmic heart conditions include atrial tachycardia, atrial flutter, atrial fibrillation, junctional rhythms, ventricular tachycardia, ventricular flutter, ventricular fibrillation, and any other non-pacemaking related arrhythmic condition which may be corrected by applying electrical shocks to the heart. Obviously then, "defibrillation" is included in the term cardioversion as a method of applying electrical shocks to the heart to defibrillate fibrillating atria or fibrillating ventricles.

Many of the known techniques, such as defibrillation in a hospital setting or defibrillation by a paramedic as part of a resuscitation program, rely upon the human detection of VF. This detection has typically been accomplished by a trained operator interpreting an ECG from an oscilloscope tracing. However, there are situations where such an approach to reversing VF is impossible or impractical. There is accordingly a great need for an electronic device able to accurately detect VF or other life threatening arrhythmias from an input ECG where such a traditional approach is unfeasible. For example, an external defibrillator could be built with an interlock to its discharge switch so that a shock can be delivered only after the presence of VF has been confirmed by a detector receiving an ECG signal from the paddles. Such a defibrillator could safely be used by even an untrained operator.

With regard to the automatic implantable defibrillator, techniques have been developed which are generally acceptable for detecting VF and discriminating between life threatening arrhythmias and other cardiac malfunctions. Yet there is considerable room for improvement with regard to detecting and discriminating VF from other non-fatal arrhythmias. Accordingly, another use for such a detector, as noted above, would be in the fully-implantable automatic defibrillator.

Previous approaches to VF detection for implantable devices have had certain drawbacks. Fundamental questions, particularly important to an automatic implantable defibrillator, relate to potential failure modes, the risks to a patient should the device reach one of these failure modes, and specifically to whether failure should occur in a passive or an active manner. Considerations of failure modes in another field, for example, have led pacer manufacturers to design pacers to resort to fixed rate pacing, an active mode, should there be a sensing failure such as caused by interference. The risk of competing with the natural heartbeat has been judged less than the risk of potential inhibition when pacing is needed.

Similar principles apply to the automatic implantable defibrillator, though simple answers do not exist. An active mode failure would result in the delivery of a shock when none is necessary, an occurrence which could be particularly unpleasant to the patient. A passive mode failure, on the other hand, would inhibit the delivery of a necessary shock, and could result in death. Obviously, failures must be minimized, but they still must be considered. In this regard, it is believed preferable that potential sensing failures lead to inherent passivity of a defibrillating device.

In many known VF detectors and automatic implantable defibrillators, the primary detection schemes would result in active mode failures unless other lockout circuitry is provided. Examples are R-wave sensors, pressure sensors, and elastomeric contraction sensors. In each case a failure in the primary sensor would have the same inherent effect as fibrillation, causing the automatic implantable device to fire, an active failure.

There is accordingly a great need for a VF detector which is accurate in its detection of VF or other life threatening arrhythmias, so that failure modes may be passive. It is toward the development of a VF detector such as this that the present invention is directed. The present invention is directed more generally to the development of an accurate, simple detector of cardiac arrhythmias which overcomes or eliminates the drawbacks of known detectors.

SUMMARY OF THE INVENTION

The present invention relates to a system for measuring the electrical activity of the heart, and which can reliably discriminate between hemodynamically efficient and inefficient arrhythmias, being particularly sensitive to ventricular fibrillation. Though presented as a part of an automatic implantable defibrillator, it should be appreciated that the present invention is not limited to this specific application. For example, and as noted above, other arrhythmias or tachyarrhythmias can easily be identified by utilizing the teachings of the present invention.

Customarily, the term electrocardiogram (ECG) implies the use of electrodes on the body surface to obtain electrical signals indicative of heart activity. The term electrogram, on the other hand, generally refers to measurements made at the surface of the heart. As used herein, "ECG" is defined broadly, and refers to any measurement of the electrical activity of the heart, notwithstanding the source or technique of the measurement.

With the present invention, VF may be detected with a degree of accuracy never before possible, and hence inherent passive failure modes can be afforded. The inventive detector enjoys operation independent from the concepts of QRS detection and heart rate calculations to maximize accuracy. As is known, these concepts are particularly difficult to defined during ventricular fibrillation. Furthermore, high-amplitude P and T-waves can inaccurately be sensed as R-waves, leading to false VF diagnosis. The inventive VF detector does not suffer from this drawback. Furthermore, the inventive VF detector has simple circuitry to minimize component count and therefore the possibility of electronic component failure, and the circuitry of the inventive VF detector is easily adaptable to low power operation.

The inventive VF detector depends for its operation upon what may be thought of as the principle of probability density function. Briefly, the probability density function defines the fraction of time, on the average, that a given signal spends between two amplitude limits. The probability density function is fully explained in the aforementioned copending application Ser. No. 787,005 and so too are several uses of the full probability density function and the probability density function sampled at two or more locations. Accordingly, these uses will not be repeated herein.

The subject invention is directed to a circuit whereby an ECG is filtered by a high pass filter, and then the so filtered ECG is used to derive the AGC control voltage for an automatic gain control circuit; the filtered ECG being further also fed to a window comparator having a predetermined window. In a second embodiment, an absolute value circuit and a level comparator take the place of the window comparator. The output of the inventive detector circuit clearly establishes whether the ECG is normal or represents an arrhythmia such as ventricular fibrillation.

In U.S. Pat. No. 3,587,563, issued to Ragsdale on June 28, 1971, a complex heart monitor is disclosed. A part of this heart monitor is a fibrillation detection circuit, and such circuit utilizes a window comparator. While some of the circuit elements appear similar to the inventive circuit, the principles of operation differ, and the inventive circuit offers significant advantages not obtainable by Ragsdale.

Of importance in the inventive circuit is the high pass filtration of the ECG. This filtration, as opposed to the low pass filtration utilized by Ragsdale, provides the ability for accurately detecting as "normal" ECG traces with large, sloping ST segments. This is particularly important in an implantable device since large, sloping ST segments are often seen from direct cardiac electrodes. Ragsdale must provide substantial additional circuitry to ensure that his circuit does not diagnose such ECG traces as fibrillations. The high pass filter in the inventive circuit eliminates the sensing difficulties encountered by Ragsdale, and ensures that large, sloping ST segments and the like are not inaccurately diagnosed as ventricular fibrillation.

Also of importance in the inventive circuit is the point from where the input determining the control voltage for the automatic gain control is taken. In the disclosed system, the AGC control voltage pick off point occurs after filtering.

In the inventive circuit, the high pass filtering (or taking the derivative) of the ECG has the effect of de-emphasizing the ST segment. Since the filtering is done before the AGC control voltage is derived, the remaining R wave will be held at constant amplitude by the AGC and a signal consisting of fixed height R waves and a minimal ST segment results. This is quite contrary to the Ragsdale circuit, where filtering (low pass) takes place after the point from which the gain control voltage is taken. Thus, the ECG and filter must be separate blocks to allow access to the unfiltered signal. More importantly, in Ragsdale, the initial application of gain control to an ECG having a large, sloping ST segment will not change the relative amplitudes of the R wave and ST segment, and in fact, the AGC may be holding the large ST segment at a constant value. The low pass filter will then substantially eliminate any remaining R wave, resulting in a signal consisting mainly of slow ST information and an erroneous diagnosis of fibrillation. To overcome this failing, Ragsdale adds additional circuitry. The inventive circuit, far more simple than that of Ragsdale, avoids the failing for which Ragsdale compensates.

It is accordingly the main object of the present invention to provide an accurate detector of cardiac activity.

Another object of the invention is to provide an apparatus for monitoring heart activity.

An added object of the invention is to provide an apparatus for monitoring heart activity, for detecting abnormalities, and for cardioverting a malfunctioning heart, when appropriate.

A further object of the present invention is to provide an efficient and accurate VF detector which is capable of implantation.

Still another object of the invention is to provide a VF detector which accurately responds to even the most difficult-to-recognize normal heart activity.

Yet an additional object of the present invention is to provide a simple VF detector capable of implantation and high diagnostic efficiency, and yet having a minimum of circuit components.

A further object of the present invention is to provide a simplified system for detecting cardiac arrhythmias including a detector utilizing a filter for taking the derivative of an ECG.

Another general object of the present invention is to provide a simple and yet reliable VF detector which, should it fail, fails in a passive mode.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

FIG. 1(a) is a tracing of a square wave given for exemplary purposes;

FIG. 1(b) is a plot of the probability density function of the wave illustrated in FIG. 1(a);

FIG. 3(a) is a typical catheter sensed ECG trace;

FIG. 3(b) is a plot of the probability density function of the ECG trace illustrated in FIG. 3(a);

FIGS. 8($b$) through 8($e$) are curves representing signals at select locations in the circuit illustrated in FIGS. 6 and 7, based upon the ECG input illustrated in FIG. 8($a$)

DETAILED DESCRIPTION OF THE DRAWINGS

Before embarking upon a detailed explanation of the inventive circuit, there follows a brief discussion of the theory of probability density.

The inventive detector system was developed as a result of the recognition that a series of measurements on the ECG known in the literature as the probability density function can be used to distinguish between normal cardiac rhythm and what can be considered rhythm in need of cardioversion. The probability density function is denoted as $K_x(X)$. If $X(t)$ is a function of time, then $K_x(X)$ can be interpreted as a function that defines the fraction of time, on the average, that $X(t)$ spends between two limits. For example, the area under $K_x(X)$ between $X=X_1$ and $X=X_2$ is the fraction of time that $X(t)$ spends between the limits $X_1$ and $X_2$. Looking at the simplified example illustrated in FIG. 1($a$), it can be seen that $X(t)$ is always either at the levels $X=B$ or $X=A$, and that the waveform spends half of its time at each one of these limits. The probability density function for this example is illustrated in FIG. 1($b$), wherein the continuous function of time $X(t)$ has been mapped into a function of the amplitude-time distribution of $X(t)$.

The inventive design, in effect, utilizes the absence of a peak at zero in the probability density function of a high pass filtered ECG as being characteristic of abnormal cardiac rhythm. By taking the derivative of the original ECG input signal (the function of the high pass filter described above), the zero peak is considerably emphasized for normal rhythms, thus enhancing the discrimination between fibrillation and normal signals. This can be seen by reference to FIGS. 2($a$) through 2($d$). In FIG. 2($a$), there is illustrated a square wave alternating between "+A" and "−B". The probability density function of this square wave is given in FIG. 2($b$), and is similar to that shown in FIG. 1($b$). Since the square wave spends no time at $X=0$, the probability density function has no peak at $X=0$. FIG. 2($c$) represents an impulse train which is developed by taking the derivative of the square wave illustrated in FIG. 2($a$). The distribution function (probability density function) of the impulse train, unlike that illustrated in FIG. 2($b$), is a unit impulse at zero, as shown in FIG. 2($d$). Thus, the effect of taking the derivative of the original square wave input and then evaluating the probability density function of the derivative is to shift peaks to $X=0$.

Figure 2A:
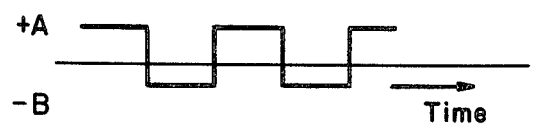
FIGS. 2(a) through 2(d) are curves illustrating an ideal example of filtering an ECG trace to move the probability density function to zero.
Figure 2B:
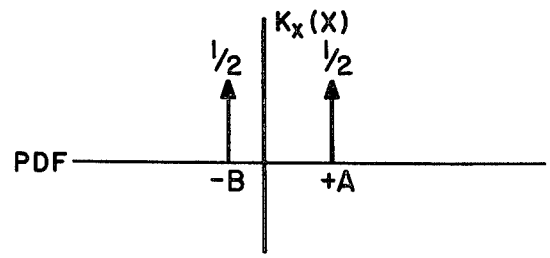
Figure 2C:
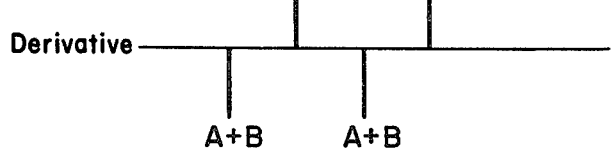
Figure 2D:
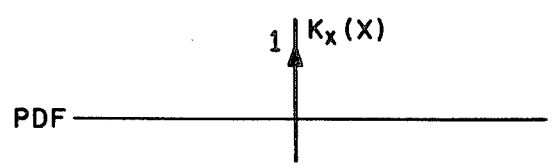
Figure 4A:
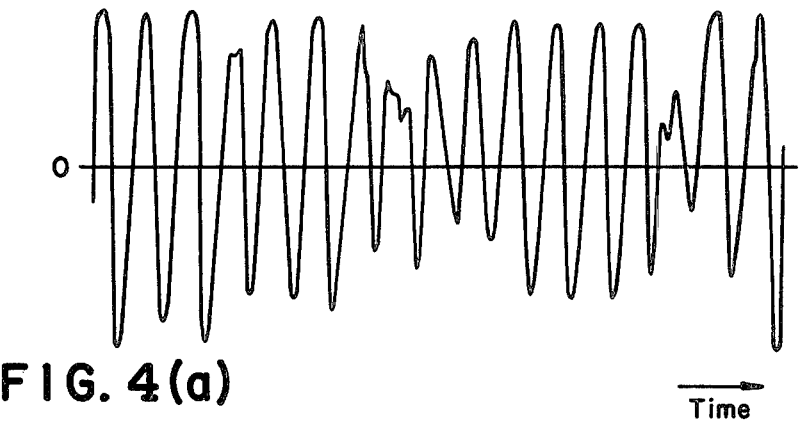
FIG. 4(a) is an ECG trace representing ventricular fibrillation after passing through the high pass filter.

As explained above, the probability density function of an ECG changes markedly between normal cardiac rhythm and ventricular fibrillation. In this regard, the attention of the reader is directed to FIG. 3($a$) which illustrates a typical (unfiltered) ECG trace, to FIG. 3($b$) which shows the probability density function of the ECG illustrated in FIG. 3($a$), to FIG. 4($a$) which illustrates an exemplary ECG trace representing filtered ventricular fibrillation, and to FIG. 4($b$) which is the probability density function of the trace illustrated in FIG. 2($a$). It will be noted that when comparing normal cardiac rhythm with ventricular fibrillation, the greatest changes occur in the respective ECG traces at $X=0$, or at the baseline of the ECG signal. Normal ECG activity is seen to have long sections of time during which the signal is constantly near the baseline while during fibrillation the signal only briefly crosses the baseline. This is markedly reflected in the probability density functions as can be seen when contrasting FIGS. 3($b$) and 4($b$).

Figure 5A:
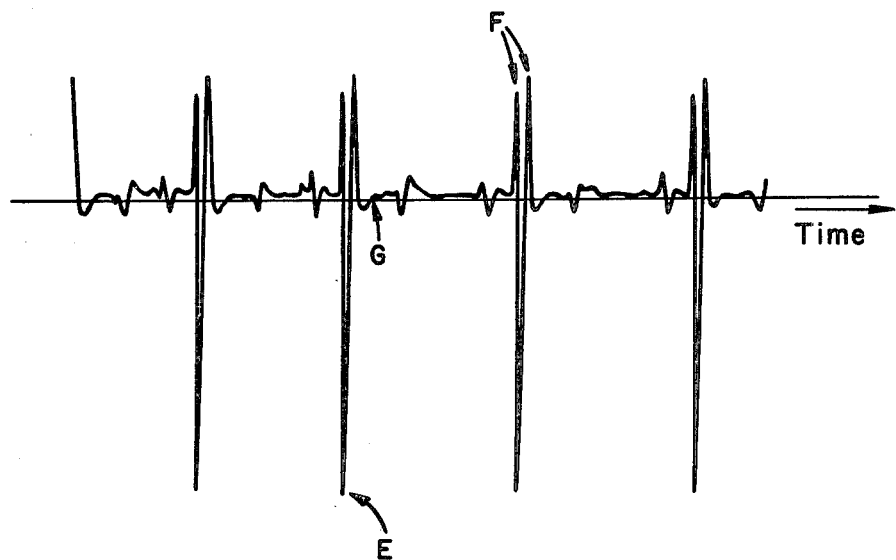
FIG. 5(a) is a curve similar to that illustrated in FIG. 3(a), but representing the ECG trace also after filtering.
Figure 5B:
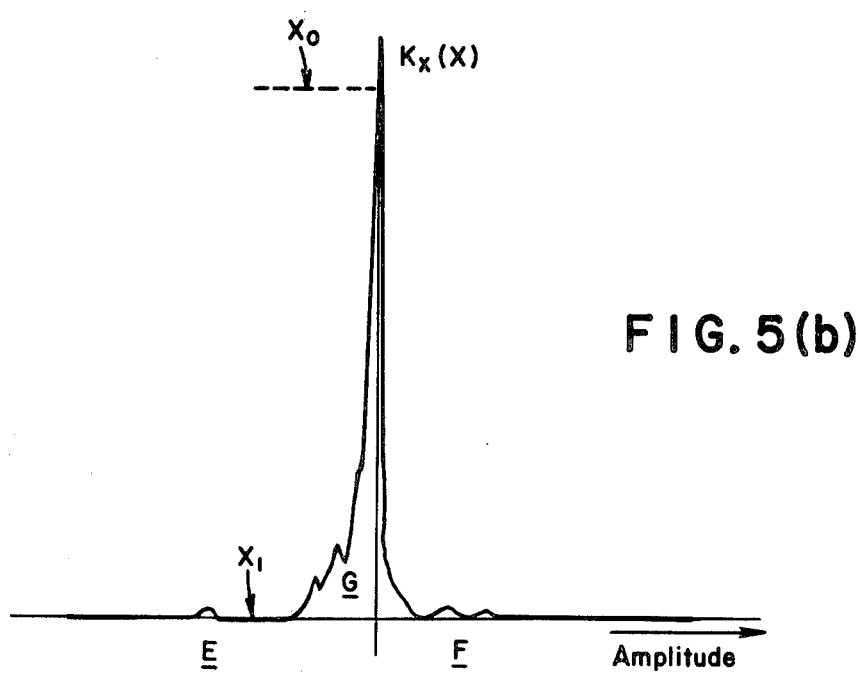
FIG. 5(b) is a probability density function similar to that shown in FIG. 3(b), but illustrating the effect of filtering the ECG of FIG. 5(a)

The contrast noted above is even more pronounced in the case of an ECG curve which has been high pass filtered. In this regard, a filtered ECG is shown in FIG. 5($a$). Indeed, the trace of FIG. 5($a$) represents the curve of FIG. 3($a$) after filtering. As can be seen, the peak "A" corresponding to the ST segment which appears in FIG. 3($b$) has been eliminated from the probability density function wave of FIG. 5($b$). Furthermore, the FIG. 5($b$) zero peak is considerably larger than that of FIG. 3($b$). Thus, the high pass filter improves the detection accuracy by enhancing the zero peak of the probability density function and thereby emphasizing the measure of the differences between VF and normal cardiac rhythm.

In the first embodiment of the present invention, an approximation to a single sample of a probability density is developed for one value of X, namely $X=0$, or at the baseline of a filtered ECG. The filter, in its most basic form, provides the derivative of the ECG. Physiologically then, sampling the probability density of the filtered ECG at $X=0$ corresponds to detecting the presence of relative isoelectric segments in the ECG. These isoelectric segments disappear during severe tachyarrhythmias such as fibrillation.

Figure 6:
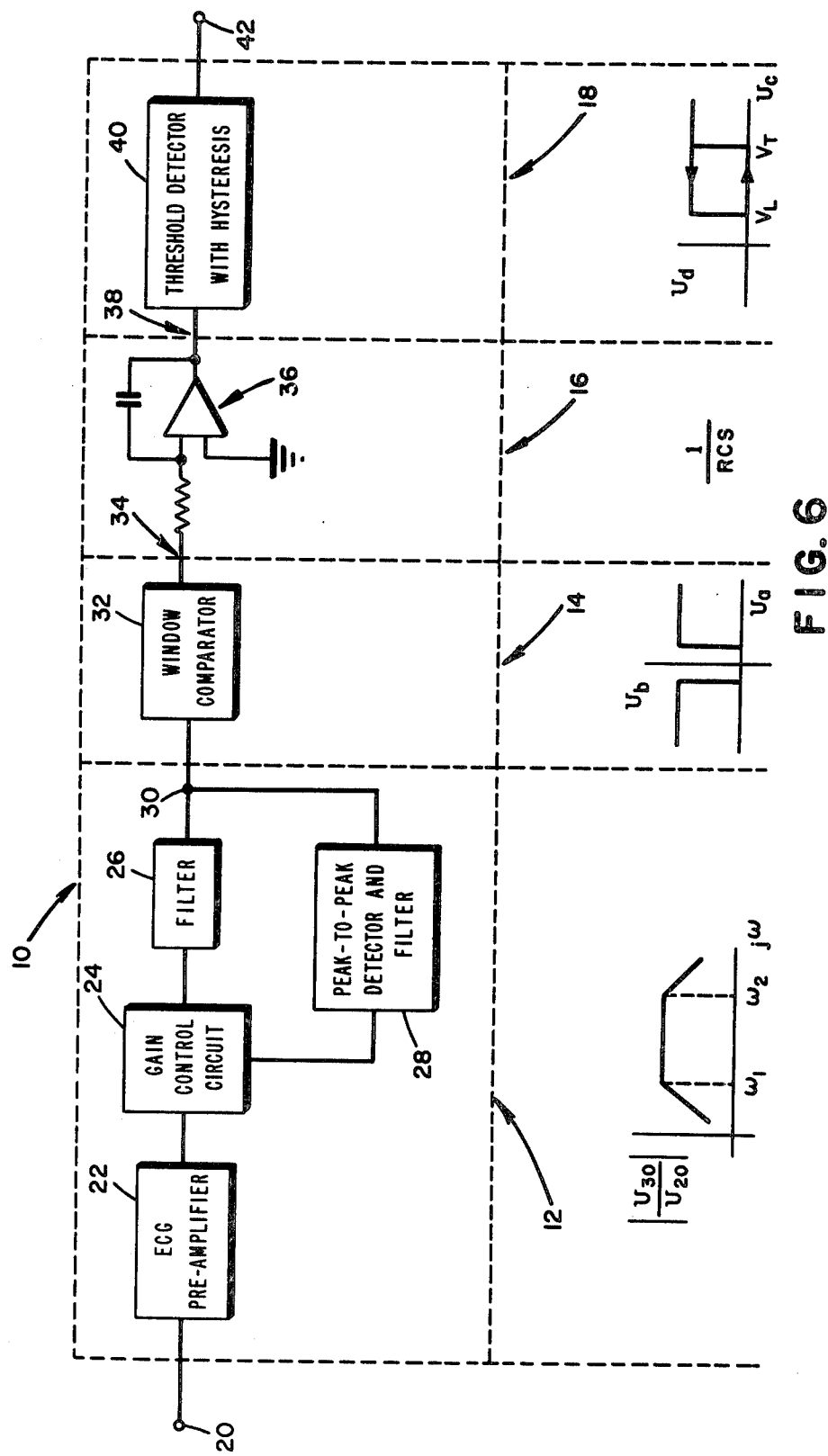
FIG. 6 is a block diagram of the VF detector forming a part of the present invention.
Figure 7:
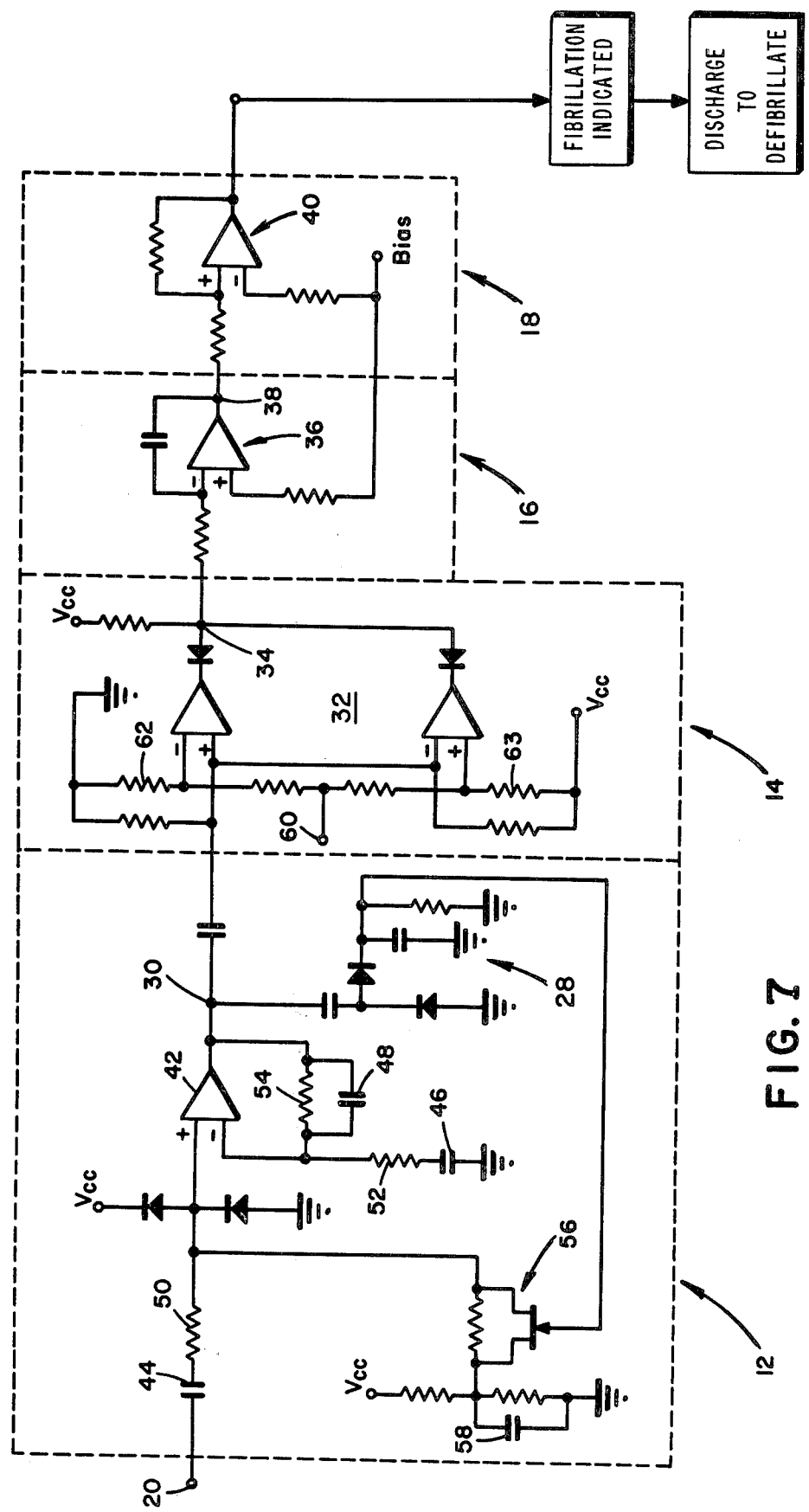
FIG. 7 is a detailed circuit schematic of the inventive detector illustrated in FIG. 6.
Figure 8:
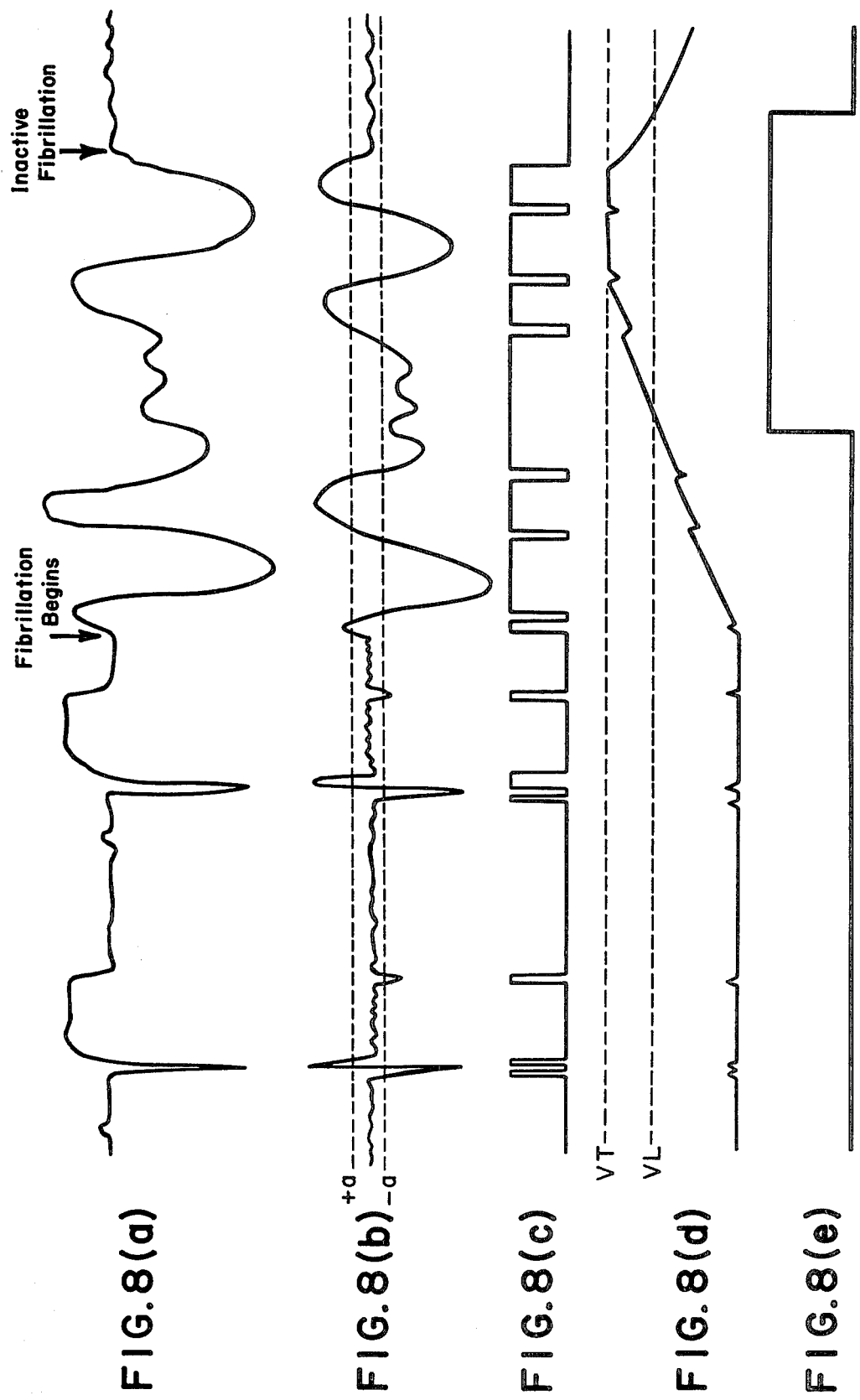
FIG. 8($a$) is a curve of an exemplary input ECG signal to the detector circuit of FIGS. 6 and 7, showing both normal cardiac rhythm and fibrillation.

The inventive detector is shown in block form in FIG. 6, and in detailed schematic form in FIG. 7; and a representative set of waveforms is illustrated in FIGS. 8($a$) through 8($e$). The detector circuit is shown generally at 10, having a first stage ECG section 12, followed by a window stage 14, integrator stage 16 and threshold detector stage 18. As illustrated, the input to the detector 10 is by way of terminal 20 which leads directly to an ECG preamplifier 22. The output from preamplifier 22 is fed to a gain control circuit 24, the AGC pick-off point of which occurs after filtration by a high pass filter 26 through a combined peak-to-peak detector and second filter 28. It should be noted that because the functions performed by the preamplifier 22, the gain control circuit 24 and the high pass filter 26 are linear functions, the order of these circuit elements can be changed. See FIG. 5, for example, where gain control precedes the preamplifier, and where the ECG preamplifier and filter are combined in a single block. Of importance, however, as noted above, is that the ECG pick-off point follows filtration.

The ECG section 12 has a bandpass filter characteristic. Most important in this bandpass characteristic is the high pass section which is designed to reject low frequency ECG components such as ST segments and to provide an approximation of the first derivative. Providing the high pass filter characteristics herein is a low-Q bandpass filter which for low frequencies, in effect, performs a differentiating function. The automatic gain control circuit 24 is provided to normalize the probability density function over a known and fixed range of amplitude. Window comparator 32 serves to detect whether the input from ECG section 12 is inside or outside a given band centered about zero level, and to issued an indicative digital output signal. Integrator 36 in stage 16 integrates the signal from window stage 14 with respect to a bias level. And in detector stage 18, a threshold detector, or comparator 40 issues a signal at terminal 42 indicative of whether the signal at 38 is above or below a given threshold level. To facilitate understanding of the simplified block diagram of FIG. 6, the respective transfer characteristics for the four discrete sections are provided immediately beneath each section.

With particular reference now to FIG. 7, it can be seen that amplifier 42 serves as the main gain block, with capacitors 44, 46 and 48, and resistors 50, 52 and 54 serving as the bandpass elements. Gain control is provided through peak-to-peak detector and filter 28, which controls N-type junction field effect transistor 56 which, in turn, shunts part of the ECG signal to ground through capacitor 58. This partial shunting results in a voltage divider effect with resistor 50. A typical endocardial electrocardiogram which would appear at terminal 20 and the corresponding output of the ECG section 12 which would appear at terminal 30 are illustrated in FIGS. 8(a) and 8(b), respectively. It should be apparent that the bandpass elements, or filter 26 in the ECG section 12, concentrate the cardiac signal to a significant degree along the time axis.

Figure 4B:
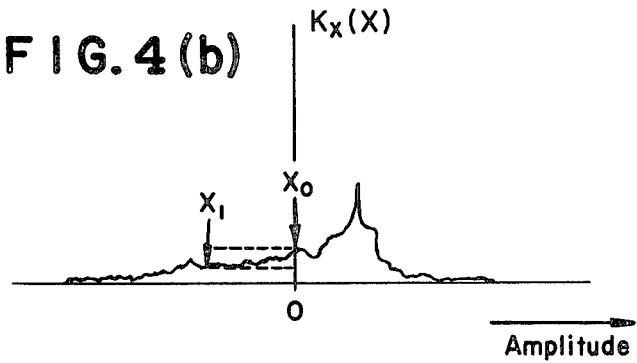
FIG. 4(b) is a curve representing the probability density function of the ECG trace illustrated in FIG. 4(a)

After initial amplification and filtering in ECG section 12, the signal at terminal 30 passes through window section 14 which comprises a window comparator 32. Window comparator 32 is designed to provide a digital signal at its output terminal 34, the sense of which depends upon whether the input to the comparator 32 lies inside or outside a band centered about a given window level introduced at terminal 60. In effect, the window serves to discriminate between high slope and low slope segments of the filtered ECG. The window level at terminal 60 is chosen at the ECG base line. The band can be seen between "+a" and "−a" in FIG. 8(b), and the resultant digital signal developed by window comparator 32 and appearing at terminal 34 can be seen in FIG. 8(c). It will be noted that the digital output of comparator 32 goes to a fixed level whenever the filtered signal leaves the designated band. The sizes of resistors 62 and 63 set the bandwidth 2a. It can also be seen in FIG. 8(c) that upon the onset of fibrillation, very little time is spent by the filtered ECG signal inside the designated band, corresponding to the lower value of the probability density function at X=0 as shown in FIGS. 1(b) and 4(b).

The digital signal appearing at terminal 34 is then integrated by integrator 36 with respect to a bias level, and produces a signal at output terminal 38 such as that illustrated in FIG. 8(d). In effect, this signal is a continuous time average of the ratio of high slope to low slope segments of the filtered ECG, where the time average is the accumulated difference in area between the in-window and out-of-window conditions of the window comparator. As can be seen, this output signal takes the form of a ramp when fibrillation begins. The output signal at terminal 38, in turn, becomes an input to the threshold detector, or comparator 40. Detector 40 then switches when the ramp signal at terminal 38 reaches a given threshold level. As can be seen in FIG. 6, hysteresis is provided in the threshold detector stage 40 for a latching function so that the ramp must fall past level VT to VL (shown in FIG. 6 on the transfer characteristic beneath detector 40) for the fibrillation detection to cease. This is indicated in FIG. 8(e) during the period of inactive fibrillation shown in FIG. 8(a) wherein the trace of FIG. 8(d) falls beneath the upper switching threshold of detector 40. Still, the output of detector 40 is high, resulting from the noted hysteresis characteristic.

It should be noted that the above-described detector provides inherent passive failure mode behavior and remains inactive if no ECG is applied. Also, the inventive detector is independent of heart rate definition and its inherent ambiguity during VF. In addition, with the high pass filtration and the subsequent gain control provided by the instant invention, many failings of the prior art have been overcome.

Figure 9:
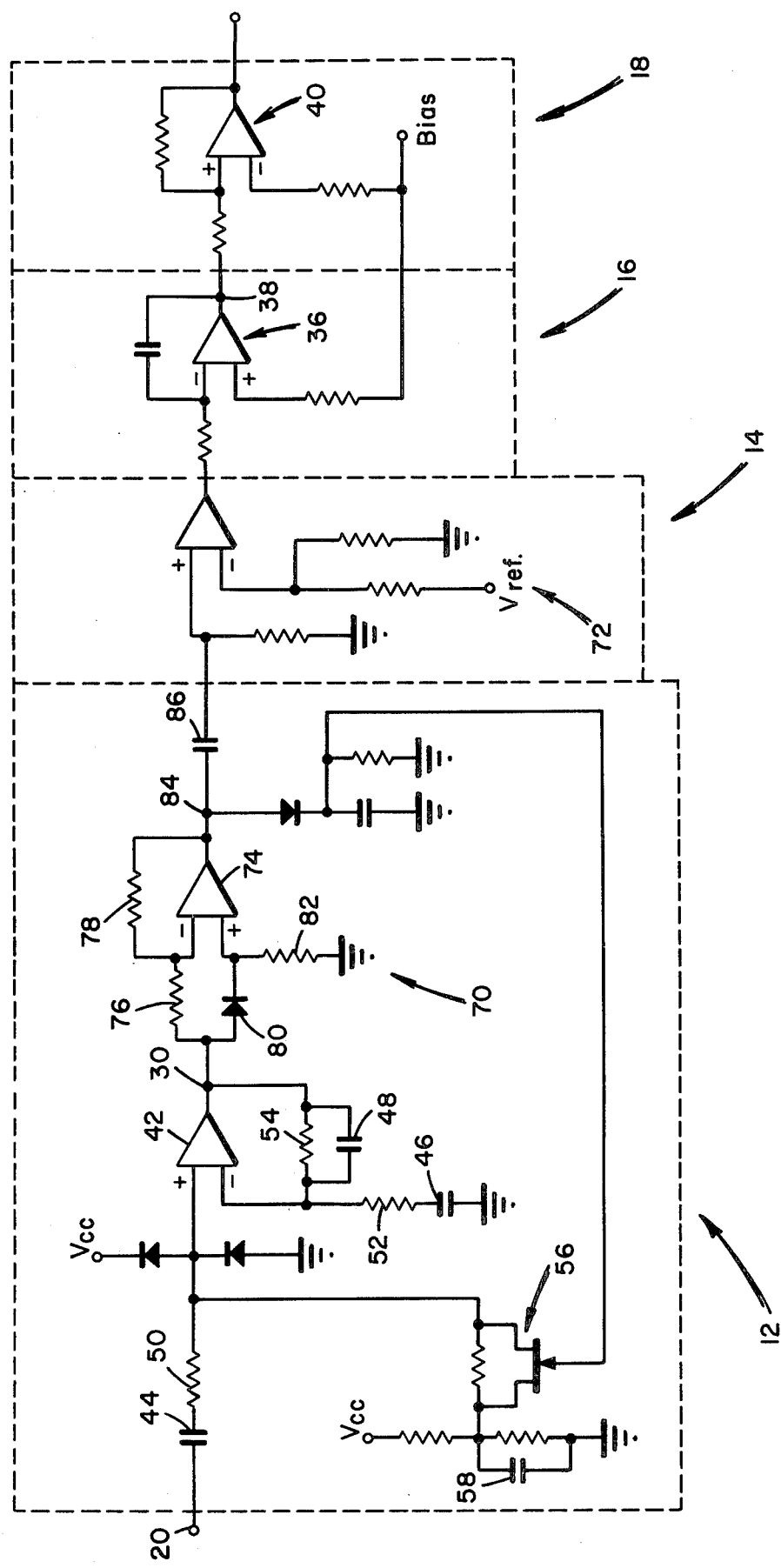
FIG. 9 is an illustration representing an alternate embodiment of the present invention.

With reference now to FIG. 9, another embodiment of the inventive detector circuit will be described. It should be readily apparent that the embodiment of FIG. 9 is in most respects identical to the embodiment illustrated in FIG. 7 and described in the preceding paragraphs. However, the peak-to-peak detector and the window comparator circuits of FIG. 7 have been replaced by an absolute value circuit 70 and a comparator circuit 72 illustrated in FIG. 9.

In FIG. 9, the output of amplifier 42 is fed to the inverting input of an operational amplifier 74 through a resistor 76. A resistor 78 of the same size as resistor 76 defines a feedback path. A diode 80 associates with the non-inverting input of operational amplifier 74, grounded through a large resistor 82. The pick-off point for the automatic gain control circuit is indicated at 84. Absolute value circuit 70 is a unity gain circuit which serves to convert the positive and negative-going input ECG signals to a representative absolute value signal in the positive-going sense.

Comparator 72 receives its input from the absolute value circuit 70 through a capacitor 86. As with the window comparator 32 of FIG. 7, the function of comparator 72 of FIG. 9 is to issue an output of a first sense if its input is below a reference voltage, and to issue an output of a second sense if its input is above a reference voltage.

With the circuit of FIG. 9, since an absolute value circuit is utilized, the peak-to-peak function becomes unnecessary. Accordingly, when contrasting FIGS. 7 and 9, it will be noted that the peak-to-peak detector capacitor and a diode have been removed.

In all other respects, the circuits of FIGS. 7 and 9 are identical in operation. Accordingly, reference should be made to the description of FIG. 7 for the detailed operation of the circuit in FIG. 9.

Above, specific examples of the present invention have been described. It should be appreciated, however, that this description has been given for purposes of illustration only, and is in no way intended to limit the scope of the present invention. Rather, it is the intention that the present invention be limited only as defined in the appended claims.

What is claimed is:

1. A circuit for detecting the state of a heart by monitoring the continuous time average of the ratio of high slope to low slope ECG segments and for effecting cardioversion if a malfunction is indicated by such time average ratio exceeding a predetermined threshold, the circuit comprising: ECG monitor means for sensing ECG signals from a heart; signal shaping means for generating the slope of the sensed ECG signals by providing an approximation of the derivative of the input ECG; means for discriminating between high slope and low slope segments; averaging means for continuously time averaging the ratio of high slope to low slope segments; threshold means for determining whether such time average ratio of high slope to low slope segments is within predetermined threshold limits indicative of normalcy; and means for effecting cardioversion if said ratio is outside said threshold.

2. The apparatus recited in claim 1, and further comprising automatic gain control means having a pick-off point at a location after said ECG signals are shaped.

3. The apparatus recited in claim 1, wherein said signal shaping means includes a high pass filter.

4. The apparatus recited in claim 1, wherein said signal shaping means is a filter having bandpass filter characteristics.

5. The apparatus recited in claim 1, wherein said discriminating means is a window comparator having a threshold band, and wherein said window comparator issues digital output signals, the sense of which is dependent upon whether shaped ECG signals lie inside or outside said threshold band.

6. The apparatus recited in claim 5, wherein said window comparator has a window level centered about the base line of said filtered ECG signals corresponding to zero slope.

7. The apparatus recited in claim 1, wherein said discriminating means includes an absolute value circuit and a level comparator.

8. The circuit recited in claim 1, wherein said means for effecting cardioversion is a pulse generator.

9. A circuit for detecting the state of a heart by monitoring the continuous time average of the ratio of high slope to low slope ECG segments and for effecting cardioversion if a malfunction is indicated by such time average ratio exceeding a predetermined threshold, the circuit comprising: ECG monitor means for sensing ECG signals from a heart; signal shaping means for generating the slope of the sensed ECG signals by providing an approximation of the derivative of the input ECG; automatic gain control means for normalizing the height of the derivative peaks, said automatic gain control means having a pick-off point at a location after the input ECG signals are shaped; means for discriminating between high slope and low slope segments; averaging means for continuously time averaging the ratio of high slope to low slope segments; threshold means for determining whether such time average ratio of high slope to low slope segments is within predetermined threshold limits indicative of normalcy; and means for effecting cardioversion if said ratio is outside said threshold.

10. The circuit recited in claim 9, wherein said signal shaping means is a high pass filter.

11. The circuit recited in claim 9, wherein said automatic gain control means includes a peak-to-peak detector.

12. The circuit recited in claim 9, wherein said discriminating means includes an absolute value circuit and a level comparator.

13. The circuit recited in claim 9 or 1, wherein said averaging means includes an integrator.

14. The circuit recited in claim 9 or 1, wherein said averaging means includes a capacitor.

15. The circuit recited in claim 9 or 1, wherein said threshold means is a comparator.

16. The circuit recited in claim 15, wherein said comparator has threshold hysteresis.

* * * * *